United States Patent [19]
Campbell, Jr. et al.

[11] Patent Number: 5,836,949
[45] Date of Patent: Nov. 17, 1998

[54] BIOABSORBABLE INTERMEDULLARY IMPLANT SYSTEM AND METHODS OF USE

[76] Inventors: Robert M. Campbell, Jr., 415 Stone Wood, San Antonio, Tex. 78216; C. Mauli Agrawal, 2215 Pinoak Knolls, San Antonio, Tex. 78248

[21] Appl. No.: 850,935

[22] Filed: May 5, 1997

[51] Int. Cl.[6] .................................................. A61B 17/72
[52] U.S. Cl. .............................................. 606/62; 606/77
[58] Field of Search ................... 606/77, 76, 62, 606/63, 64, 86, 99, 100, 104

[56] References Cited

U.S. PATENT DOCUMENTS

| | | | |
|---|---|---|---|
| 4,756,307 | 7/1988 | Crowninshield | 606/77 |
| 5,281,226 | 1/1994 | Davydov et al. | 606/62 |
| 5,514,137 | 5/1996 | Coutts | 606/62 |
| 5,700,267 | 12/1997 | Urbanski | 606/86 |

*Primary Examiner*—Guy V. Tucker
*Attorney, Agent, or Firm*—Jenkens & Gilchrist

[57] ABSTRACT

The invention is of a family of bioabsorbable intermedullary rods, implantation systems and associated methodologies for implantation. Applicant's invention permits its users to use intermedullary rods when indicated for fracture fixation, yet avoid complications of presently available steel rods, including the post-utility presence of implants after a bone has healed.

7 Claims, 5 Drawing Sheets

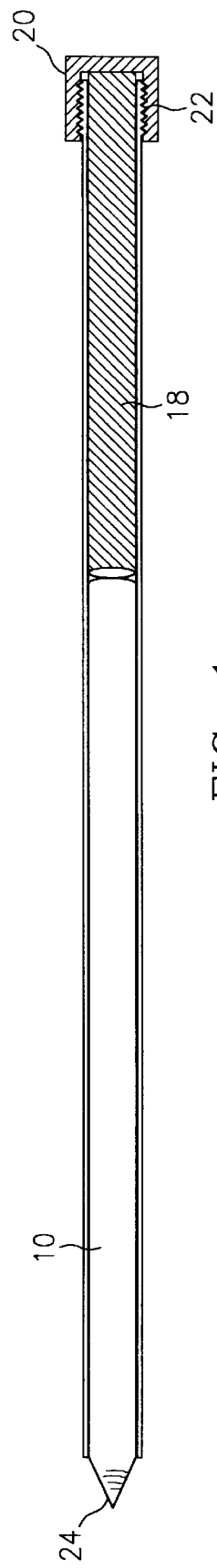
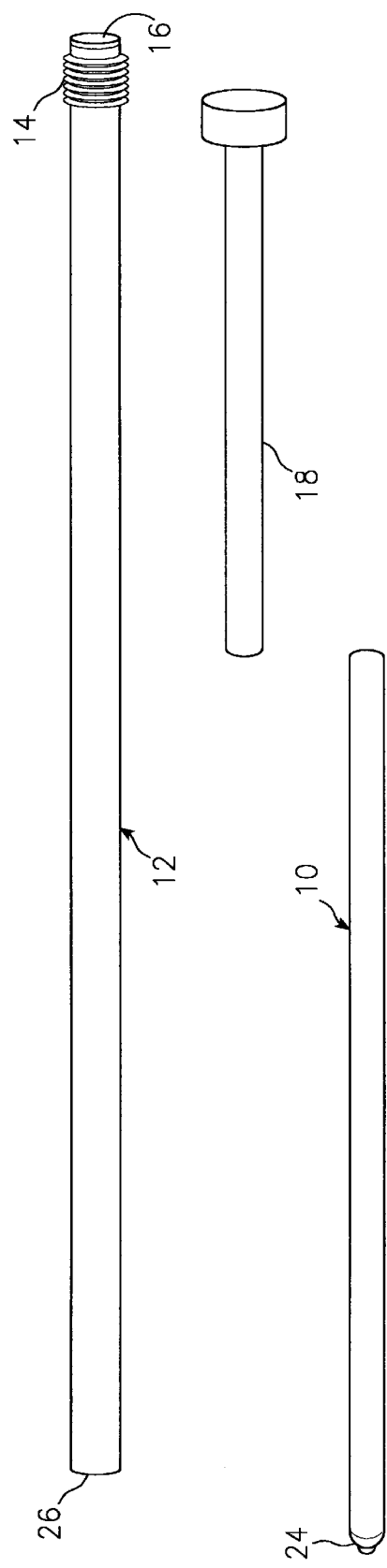
FIG. 1
FIG. 2

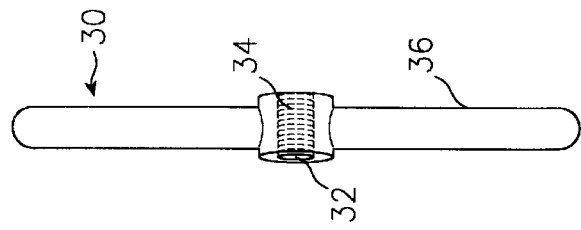
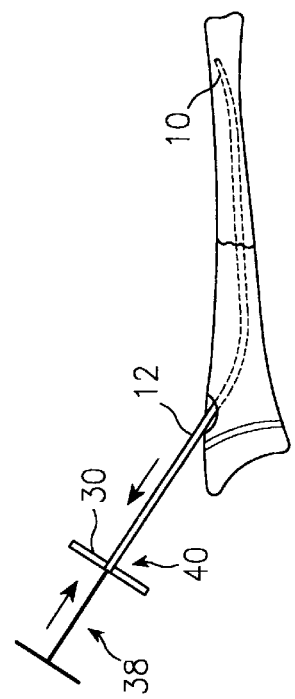
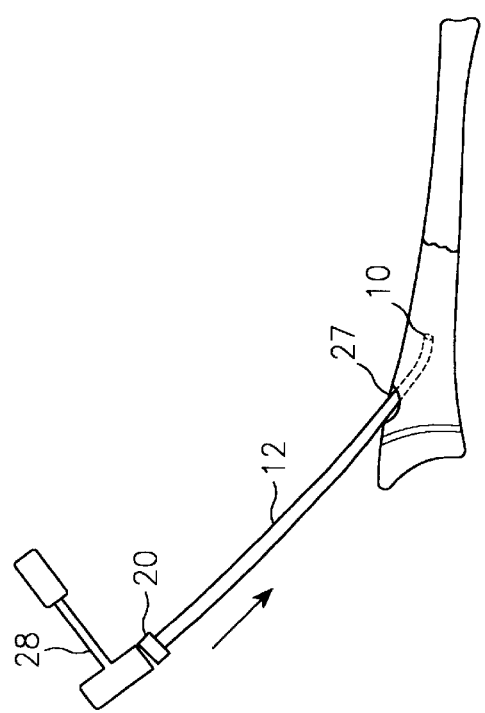

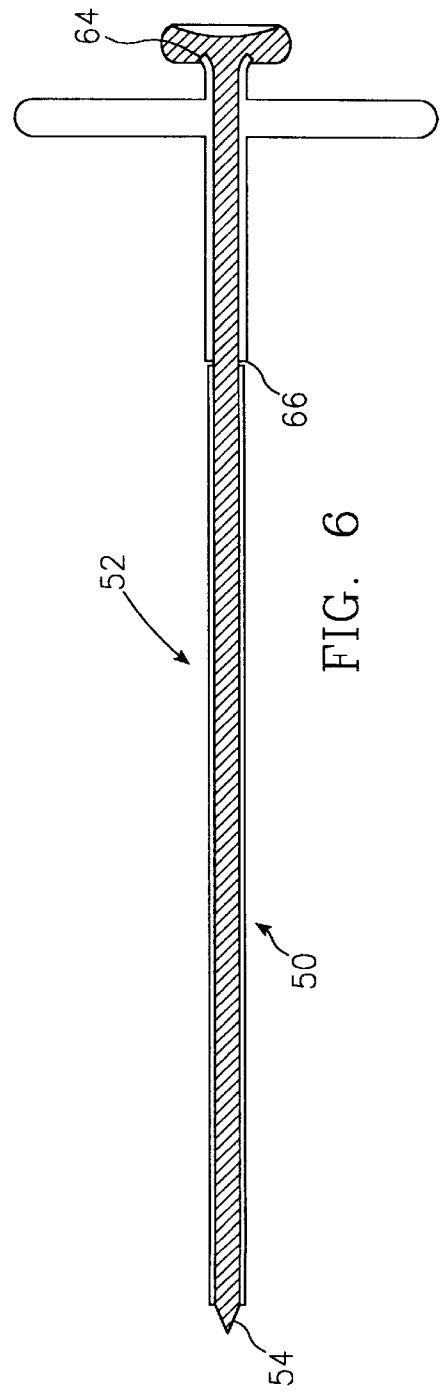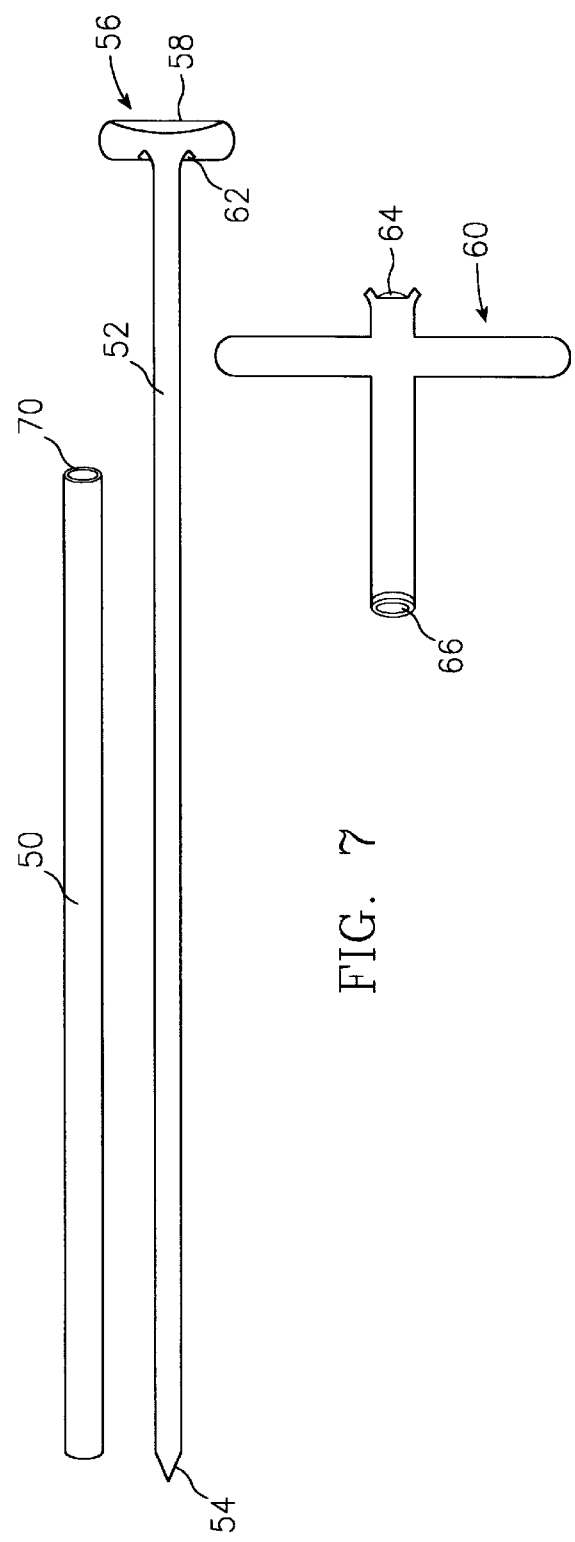

BIOABSORBABLE INTERMEDULLARY IMPLANT SYSTEM AND METHODS OF USE

BACKGROUND OF THE INVENTION

1. Field of the Invention

Applicant's invention relates to orthopedic intervention in osseous fractures, and more specifically to fracture fixation through use of implantable reinforcement members.

2. Background Information

The present treatment of bone fractures, particularly fractures of long bones, often involves the implantation of a metal rod in the intermedullary canal. The metal rod servers to immobilize the two (or more) segments of bone and to provide rigidity for the entire bone structure as the fracture mends. Metal screws are often also involved in fracture fixation.

A problem with the use of metal rods and screws in fracture fixation includes the fact that (unless subsequently removed through further, expensive and painful surgery) the implants remain long after the need for them has passed. Long-term presence of metallic screws may be a source of pain for recipients. Also, metal rods, over time, may predispose a long bone to complex subsequent fractures.

Despite the complications associated with using metallic rods and screws in fracture fixation, the only presently-available alternatives are less efficacious at best, and exchange one set of complications for others. One alternative involves using full casts. Under the best of circumstances, the complete limb immobilization imposed by casts causes muscle atrophy. Also, casts are very uncomfortable and involve hygienic challenges. Under less ideal circumstances, a difficult fracture may not heal, may angulate, or may shorten, even with the best immobilization provided by casts, and may subsequent metal fixation of the fracture.

Despite the complications involved, when use of a metal rod and/or screws is indicated, there simply are no equally efficacious treatment options. Therefore, orthopedists and their patients would be best served, not by the elimination of orthopaedic rod and screw systems, but by refinement of the involved implements whereby the problems with "retained hardware" are avoided.

SUMMARY OF THE INVENTION

It is an object of the present invention to provide a novel orthopaedic treatment implement for the treatment of bone fractures.

It is another object of the present invention to provide an improved design for intermedullary rods used in the treatment of bone fractures.

It is another object of the present invention to provide an improved design for intermedullary rods used in the treatment of bone fractures, which rods obviate the complications associated with long-term residence of rods in bone structures.

It is another object of the present invention to provide an improved design for intermedullary rods used in the treatment of bone fractures, which rods obviate any need for post-implantation removal after healing of fractures.

It is another object of the present invention to provide an improved design for bioabsorbable intermedullary rods for use in the treatment of bone fractures.

In satisfaction of these and related objectives, Applicant's present invention provides a family of bioabsorbable intermedullary rods, implantation systems and associated methodologies. Applicant's invention permits its users to use intermedullary rods when indicated, yet avoid complications of presently available steel rods, including the post-utility presence of implants after a bone has healed.

BRIEF DESCRIPTION OF THE DRAWINGS

FIG. 1 is an elevational side view of the intermedullary rod 10, sleeve inserter 12 and stylet 18 of the first described embodiment of the present invention.

FIG. 2 is an exploded elevational side view of the components of FIG. 1.

FIG. 3 depicts the introduction into a long bone of the assemblage shown in FIG. 1.

FIG. 4 is an elevational side view of the withdrawal handle 30 used in the first described embodiment of the present invention.

FIG. 5 depicts the withdrawal of the sleeve inserter 12 after longitudinal positioning of rod 10, using plunger stylet 38 to maintain proper positioning of rod 10.

FIG. 6 is an elevational side view of cannulated rod 50 and rigid stylet 52 of the second described embodiment of the present invention.

FIG. 7 is an exploded side view of the components shown assembled in FIG. 6.

DETAILED DESCRIPTION OF THE PREFERRED EMBODIMENT

Figure 8:
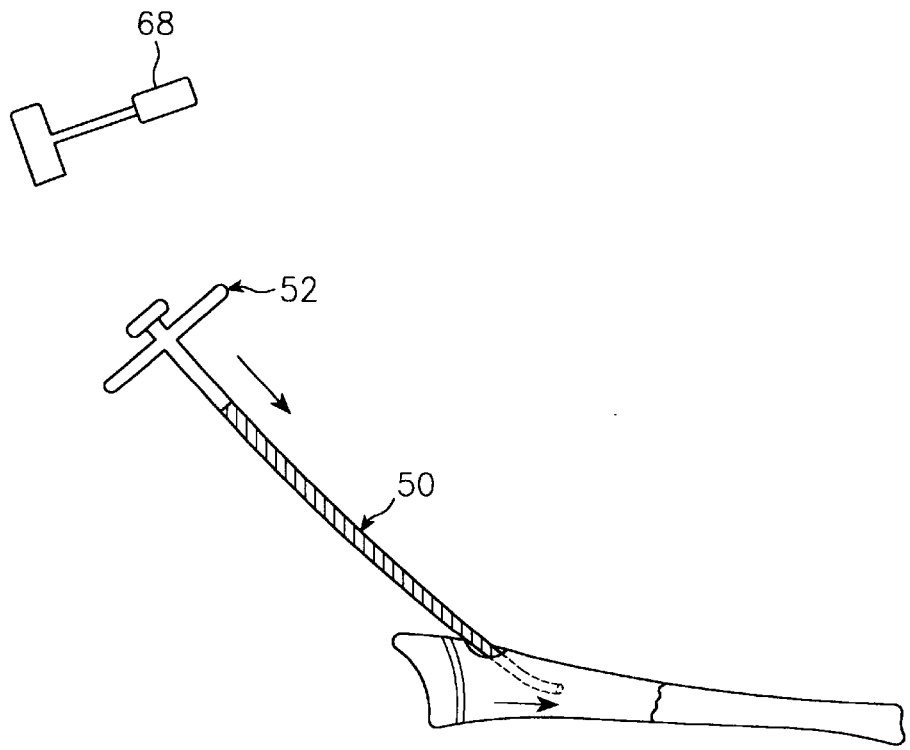
FIG. 8 depicts the introduction into a long bone of the assemblage shown in FIG. 6.

Referring to FIGS. 1 and 2, a first embodiment of the present invention includes a solid, bioabsorbable. intermedullary rod 10. The purpose of rod 10 relates to its implantation in intermedullary canals of fractured or otherwise weakened bones which require reinforcement during the healing process. Rod 10 selected for the present system is constructed of a bioabsorbable material, so that rod 10 will, over time, simply be absorbed by the body. This means that there will be no foreign object left in the bone after the need for it passes. To accelerate absorption, rod 10 is of a somewhat more slender design than the counterpart steel rods which are of the prior art.

Using a bioabsorbable rod 10, especially of a relatively small cross section, is highly beneficial for the just-stated reasons, but implantation by conventional methods relating to rod implantation is not practicable. Rod 10 is too pliable to be driven into an intermedullary canal as would be a conventional steel rod. The system of the present invention is unique in first making practical the use of bioabsorbable intermedullary rods.

Referring still to FIGS. 1 and 2, according to the present invention, rod 10 is initially placed, in telescopic fashion, in a distal portion a metallic or resilient plastic tubular member ("sleeve inserter 12"). Sleeve inserter 12 is designed with external threads 14 at its proximal end 16.

A stylet 18 is sized and shaped to extend telescopically through the open, proximal end 16 of sleeve inserter 12. Stylet 18 is provided with an integral stylet cap 20 which has internal threads 22 which are configured to mate with threads 14 of sleeve inserter 12.

The dimensions of rod 10, sleeve inserter 12 and stylet 18 are such that the distal, pointed tip 24 of rod 10 extends slightly beyond the distal end 26 of sleeve inserter 12.

Referring to FIG. 3, once configured, the combined rod 10, sleeve inserter 12 and stylet 18 are driven length-wise into the intermedullary canal of a recipient bone, through an entry hole which will have been drilled by conventional means. A hammer 28 is typically used to impact the stylet cap 20 and drive the sleeve inserter 12 and rod 10 into position.

Referring to FIGS. 4 and 5, once rod 10 (albeit still inside sleeve inserter 12) is placed longitudinally in the desired position in the bone, stylet cap 20 is disengaged from proximal end 16 of sleeve inserter, and stylet 18 is withdrawn. Withdrawal handle 30 is then substituted for stylet cap 20 at the proximal end 16 of sleeve inserter 12. Withdrawal handle 30 provides a T-handle structure as a grasping hold for sleeve inserter 12. Withdrawal handle 30 included a central orifice 32 which is internally threaded with threads 34 and from which extend handles 36. Threads 34 are configured for mating with threads 14 of sleeve inserter 12.

Once withdrawal handle 30 is attached to sleeve inserter 12, plunger stylet 38 is inserted telescopically into the proximal end 16 of sleeve inserter 12 until the distal end 40 of plunger stylet 38 rests against rod 10. The system's user then withdraws sleeve inserter 12 using withdrawal handle 30 to apply the withdrawing force to inserter 12, while applying a suitable opposing force to rod 10 through plunger stylet 38 to maintain rod 10 in the desired longitudinal position in the bone, despite the longitudinal movement of the sleeve inserter 12 around it.

Obviously, plunger stylet 38 must be of sufficient length to allow complete withdrawal of sleeve inserter 12 from the bone with plunger stylet 38 still in contact with rod 10. Once sleeve inserter 12 has been withdrawn from the patient, plunger stylet 38 may also be removed, and appropriate closure, or other orthopedic procedures may follow.

Also, the sleeve inserter 12 can be inserted with a steel or plastic stylet, then, once in place, the stylet can be withdrawn and the bioabsorbable rod 10 inserted. The sleeve inserter 12 is then withdrawn with the bioabsorbable rod 10 remaining in the bone through action of the plunger stylet 38.

Referring to FIG. 6, another embodiment of the present invention is based upon a cannulated rod 50. Like rod 10, rod 50 is fabricated of bioabsorbable materials, but is in the form of a hollow tube, rather than a solid rod, to accommodate a different implantation system.

In this second embodiment of the present invention, rod 50 is telescopically received exteriorly onto a rigid stylet 52. Rigid stylet 52 includes a distal tip 54 which is suitable tapered to act as a trocar.

Referring in combination to FIGS. 6 and 7, the proximal end 56 of stylet 52, in the preferred embodiment, is fashioned into a stylet cap 58 which is to serve as the striking surface when using a hammer 68 to drive stylet 52 into position as will be described hereafter. For anticipated ease of manufacturing as well as sterilization, T-handle attachment 60 is designed as a separate part in this system. The distal face 62 of stylet cap 58 and proximal end 64 of T-handle attachment 60 are configured into a bayonet-like locking system for securing the two components during use, but allowing their easy disengagement otherwise. The distal end 66 of T-handle attachment 60 is configured to serve as a shoulder which contacts, and transmits the longitudinal thrust applied to stylet 52, to the proximal end 70 of rod 50.

Figure 9:
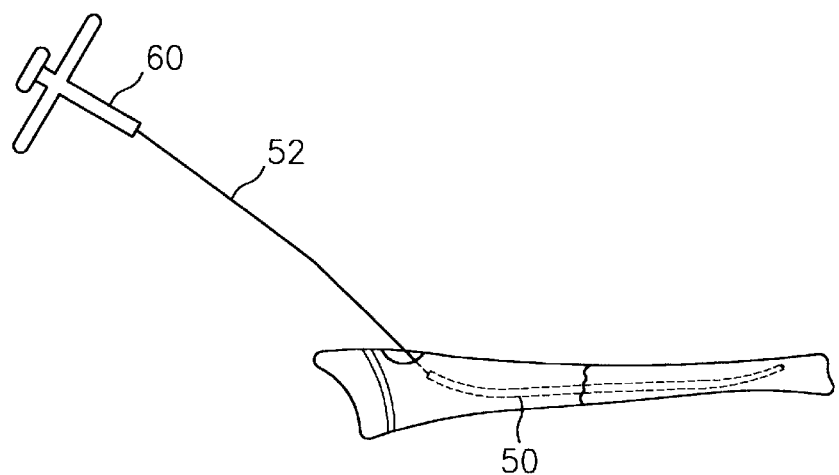
FIG. 9 depicts the withdrawal of the rigid stylet 52 after longitudinal positioning of rod 50.

Referring to FIGS. 8 and 9, as with the first embodiment of the present invention described above, stylet 52, with rod 50 loaded thereon, is driven into position using a hammer 68. Once stylet 52 has been advanced to the point where rod 50 is longitudinally in place, stylet 52 is withdrawn leaving rod 50 in position.

Because of friction between rod 50 and the surrounding tissues, there is no expectation that anything comparable to plunger stylet 38 of the first embodiment will be necessary in this second embodiment to insure that rod 50 remains in position as stylet 52 is withdrawn. Stylet 52 will simply slide from the interior hollow of rod 50.

Figure 10:
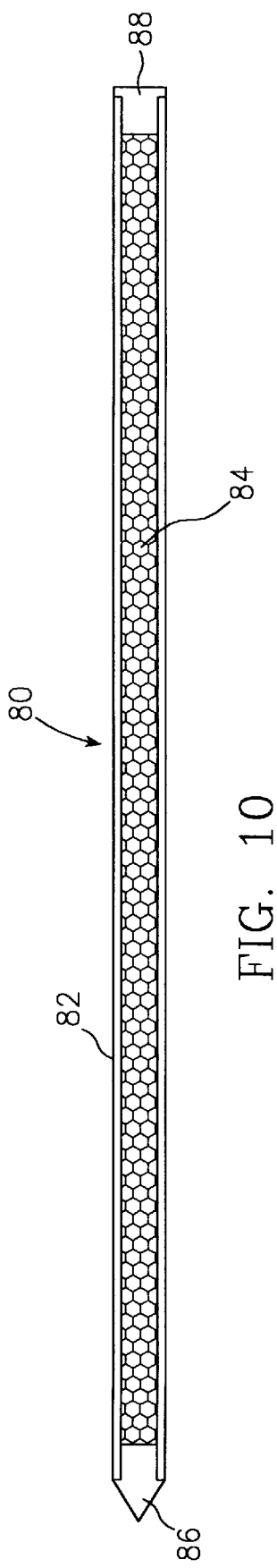
FIG. 10 is an elevational side view of intermedullary rod 80.

Referring to FIG. 10, a third embodiment of the present invention varies from the first embodiment only with respect to the nature of the intermedullary rod. Intermedullary rod 80 is a composite structure which includes a very thin outer tube (or sheath) 82 which is fabricated of bioabsorbable material. Tightly packed inside tube 82 are "bone crystals" 84 which may be hydroxyapatite crystals, tricalcium phosphate, natural coral, ALLOGRAFT BONE, BIO-GLASS materials and/or other bioabsorbable materials which are approved by FDA for implantation. A bioabsorbable distal trocar tip 86 is inserted at the distal end of rod 80, and a proximal plug 88 is inserted in the proximal end of rod 80. Both items 86 and 88 serve to contain the bone crystals 84 inside tube 82, but respectively also serve to penetrate tissues as rod 80 is advanced into a bone, and as an abutment for stylet 18 and plunger stylet 38 in their respective uses during implantation.

The structure of rod 80 yields a quite rigid structure which quite adequately supports a bone during healing. The advantage of constructing the bulk of an intermedullary rod of bone crystals lies in the resulting minimalization of materials which are foreign to bone tissues and which are, accordingly, absorbed very rapidly.

Figure 11:
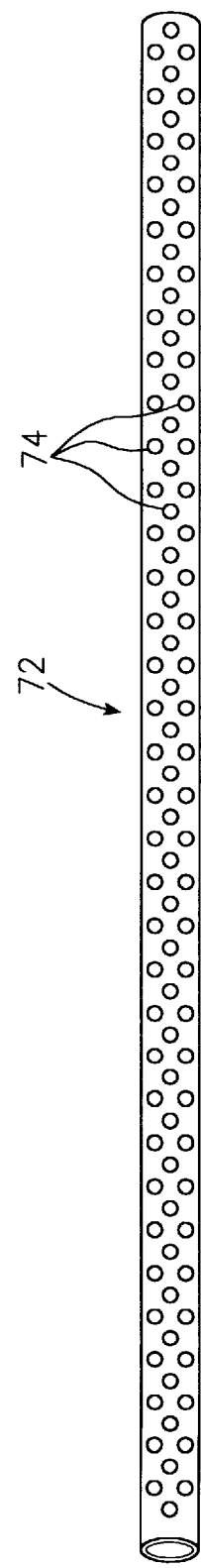
FIG. 11 is an elevational side view of fenestrated intermedullary rod 72.

Referring to FIG. 11, an alternative embodiment of an intermedullary rod useful according to the present invention is found in a variation of rod 50. Rod 72 is, like rod 50, a hollow tube, but is fashioned with numerous fenestrations 74. This structure is believed to even further accelerate the absorption process, because a greater, cumulative surface area is provided on which enzymes will act in the absorption process. The fenestrated rod 74 can also be placed with bone crystals to increase its strength.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. An orthopedic intermedullary rod system comprising:
   an elongate intermedullary rod member, constructed of bioabsorbable material;
   a rod carrier member which is configured for telescopic engagement with said intermedullary rod member substantially along its entire length, said rod carrier member being constructed of a substantially rigid material;
   force application means attached to said rod carrier member for transmitting forces to said rod carrier, and through said rod carrier to said intermedullary rod member, for moving said rod carrier member and said intermedullary rod member along their longitudinal lengths.

2. The system of claim 1 wherein said rod carrier member is an elongate insertion sleeve which is sized and shaped for telescopic reception of said intermedullary rod member in an interior sleeve hollow, said insertion sleeve having a first sleeve end and a second sleeve end, said first sleeve end having a rod ejection opening which opens into said sleeve hollow, said rod ejection opening being of a size and shape for allowing passage of said intermedullary rod member therethrough.

3. The invention of claim 1 wherein said intermedullary rod member comprises a tubular member which defines an interior hollow, said interior hollow containing a particulate bioabsorbable material comprising a substantial compliment of bone crystal material.

4. The invention of claim 2 wherein said intermedullary rod member comprises a tubular member which defines an interior hollow, said interior hollow containing a particulate bioabsorbable material comprising a substantial compliment of bone crystal material.

5. The system of claim 2 further comprising thrusting means movably engagable with said insertion sleeve for moving said intermedullary rod member from said insertion sleeve, through said rod ejection opening.

6. The system of claim 1 wherein said intermedullary rod member is an elongate tubular member, and said rod carrier member is an elongate stylet which is sized and shaped for telescopic reception of said intermedullary rod member thereon.

7. An orthopedic intermedullary rod system comprising:
an elongate intermedullary rod member which is fabricated of a flexible, bioabsorbable material;
an elongate insertion sleeve which is sized and shaped for telescopic reception of said intermedullary rod member in an interior sleeve hollow, said insertion sleeve having a first sleeve end and a second sleeve end, said first sleeve end having a rod ejection opening which opens into said sleeve hollow, said rod ejection opening being of a size and shape for allowing passage of said intermedullary rod member therethrough; and
thrusting means movably engagable with said insertion sleeve for moving said intermedullary rod member from said insertion sleeve, through said rod ejection opening.

* * * * *

UNITED STATES PATENT AND TRADEMARK OFFICE
CERTIFICATE OF CORRECTION

PATENT NO. : 5,836,949
DATED : November 17, 1998
INVENTOR(S) : Robert M. Campbell, Jr. et al It is certified that error appears in the above-identified patent and that said Letters Patent is hereby corrected as shown below:

On the title page,

At [54] - In the title, please substitute "INTRAMEDULLARY" for "INTERMEDULLARY".

At [57] - In the abstract, in the first and fourth line, please substitute the word "intramedullary" for "intermedullary".

In column 1, lines 1, 13, 51, 54, 59, 64, and 67, please substitute the word "intramedullary" for "intermedullary".

In column 2, lines 3, 8, 32, 34, 41, 43, 56, and 59, please substitute the word "intramedullary" for "intermedullary".

In column 3, line 8, please substitute the word "intramedullary" for "intermedullary".

In column 4, lines 17 (twice), 34, 39, 58, 59, 62, and 67, please substitute the word "intramedullary" for "intermedullary".

In column 5, lines 2, 6, 11, 13, and 18, please substitute the word "intramedullary" for "intermedullary".

UNITED STATES PATENT AND TRADEMARK OFFICE
CERTIFICATE OF CORRECTION

PATENT NO. : 5,836,949

DATED : November 1998

INVENTOR(S) :

It is certified that error appears in the above-identified patent and that said Letters Patent is hereby corrected as shown below:

In column 6, lines 1, 3, 6, 8, 9, 12, 18, and 20, please substitute the word "intramedullary" for "intermedullary".

Signed and Sealed this

Twenty-fifth Day of May, 1999

Attest:

Q. TODD DICKINSON

*Attesting Officer*  Acting Commissioner of Patents and Trademarks